US005602927A

United States Patent [19]

Tamamura et al.

[11] Patent Number: 5,602,927

[45] Date of Patent: Feb. 11, 1997

[54] VEHICLE INTERNAL NOISE REDUCTION SYSTEM AND THE METHOD THEREOF

[75] Inventors: Manpei Tamamura, Ohta; Hiroshi Iidaka, Tokyo; Eiji Shibata, Oura, all of Japan

[73] Assignee: Fuji Jukogyo Kabushiki Kaisha, Tokyo, Japan

[21] Appl. No.: 358,390

[22] Filed: Dec. 19, 1994

[30] Foreign Application Priority Data

Dec. 28, 1993 [JP] Japan .................................. 5-334704

[51] Int. Cl.$^{6}$ ............................ A61F 11/06; H03B 29/00

[52] U.S. Cl. ................................ 381/71; 381/94; 381/86

[58] Field of Search ................................ 381/71, 72, 94, 381/106, 86

[56] References Cited

U.S. PATENT DOCUMENTS 5,251,262 10/1993 Suzuki et al. ............................ 381/71

5,426,704 6/1995 Tamamura et al. ....................... 381/71

*Primary Examiner*—Curtis Kuntz
*Assistant Examiner*—Duc Nguyen
*Attorney, Agent, or Firm*—Beveridge, DeGrandi, Weilacher & Young, L.L.P.

[57] ABSTRACT

A vehicle internal noise reduction system and the method thereof for reducing a noise sound by producing a canceling sound from a speaker based on a tap value formed and updated in an adaptive filter, the system and the method characterized in forming the tap value of the adaptive filter by convoluting a filter coefficient having a similar band pass characteristic to a frequency characteristic of the speaker into the tap value formed by the adaptive control of the adaptive filter for the purpose of operating the noise reduction system stably without causing distortion or divergence in the system.

4 Claims, 4 Drawing Sheets

VEHICLE INTERNAL NOISE REDUCTION SYSTEM AND THE METHOD THEREOF

BACKGROUND OF THE INVENTION

The present invention relates to a noise reduction system and for a passenger compartment of automotive vehicle and method of positively generating a sound from a sound source to cancel the vehicle internal noise.

Japanese Patent Application No. Toku-Kai-Hei 3-178846 discloses a noise reduction technique for reducing noise by means of controlling a tap value of an adaptive filter to generate a canceling sound with a reversed phase by an output of a microphone which is disposed at a position where a noise is to be reduced and by a signal to compensate a transmission characteristic of the propagation path of a signal from the adaptive filter to the microphone, The noise reduction apparatus of the above prior art makes an adaptive control by recording in a transmission characteristic compensation section the transmission characteristics of a propagation path where the speaker transforms a signal from the adaptive filter into a sound wave and the sound wave propagates from the speaker to the microphone.

In the noise reduction system according to the prior art there is a disadvantage that in case where noises generated from the noise source contain frequency components which do not exist in the frequency characteristic of the speaker of the system, the noise reduction becomes unstable. In this case, the adaptive filter performs an adaptive control and transmits a canceling signal for canceling these noises out of the frequency band of the speaker.

However, the canceling signal generated from the adaptive filter is cut by the speaker and is not propagated into the space. Therefore, the error signal of the frequency component out of the band is feedback in spite of performing an adaptive control.

Because of this feedback error signal, the adaptive filter operates so as to output a signal with further larger amplitude, and as a result a distortion is caused by a fluctuation of the amplifier driving the speaker, and when it goes worse the adaptive control system would be diverged.

SUMMARY OF THE INVENTION

In view of the foregoing disadvantage, it is an object of the present invention to provide a vehicle internal noise reduction system which can perform a stable adaptive control with respect to noises.

To achieve the above object, the internal noise reduction system according to the present invention is furnished with:

filter coefficients recording means for recording a filter coefficient having a similar band pass characteristic to the frequency characteristic of the speaker; and convolution means for reading the filter coefficient from the filter coefficients recording means and for convoluting the filter coefficient read from the filter coefficients recording means into the tap value formed in the adaptive filter so as to delete a frequency component not existing in the frequency characteristic of the speaker from the canceling sound for the purpose of operating the system in a stable manner without causing distortion or divergence in the system.

In the vehicle internal noise reduction system thus constituted, the filter coefficients recording means record the filter coefficients having band pass characteristics similar to the frequency characteristics of the speaker. On the other hand, the convolution means convolute the filter coefficients recorded in the filter coefficients recording means into the tap value of the adaptive filter. As a result the signal of the frequency band rendering the system unstable is cut (not formed) and stable operation of the noise reduction system can be achieved.

DESCRIPTION OF THE PREFERRED EMBODIMENTS

Figure 1:
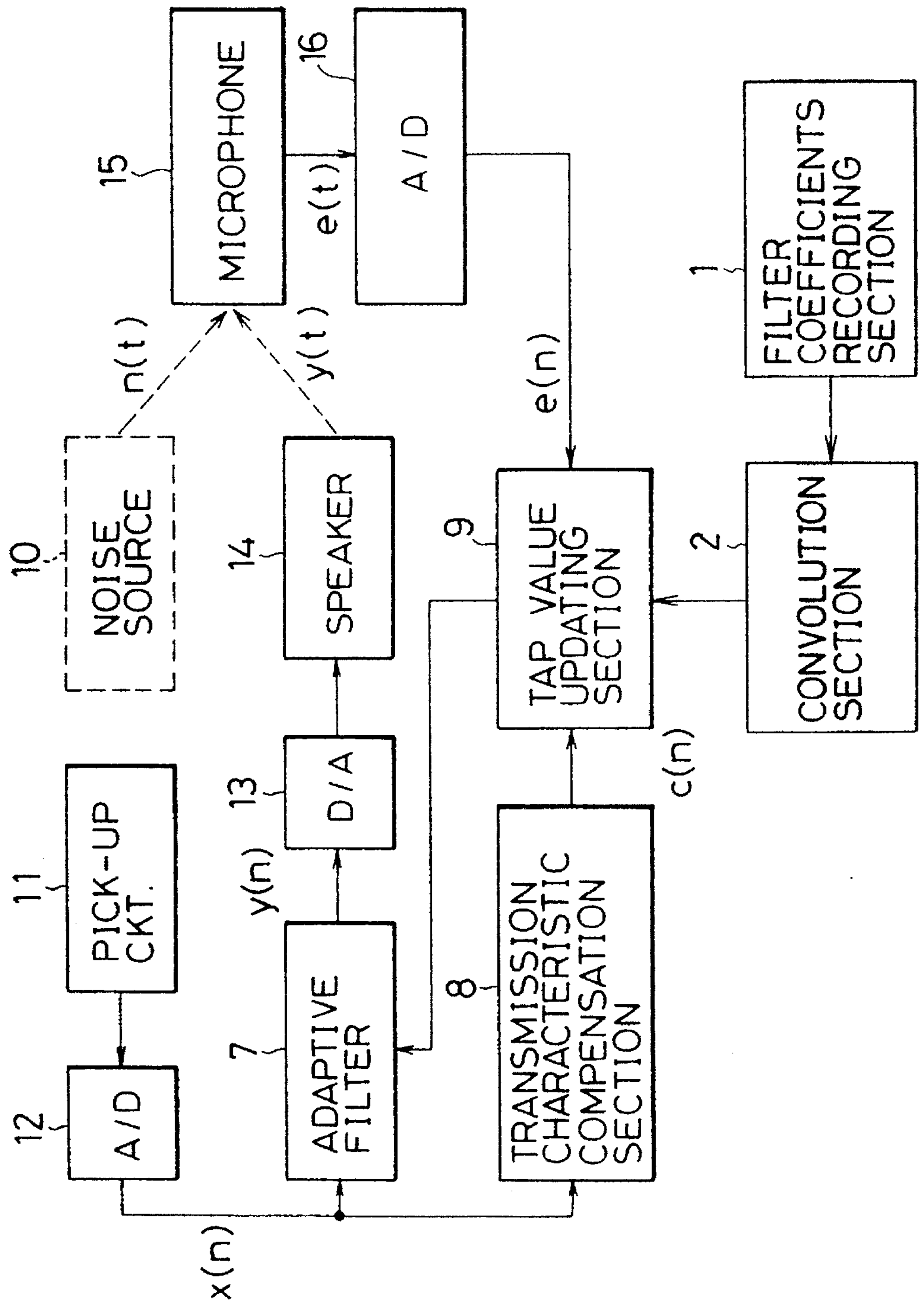
FIG. 1 is a schematic diagram showing an embodiment according to the present invention.

Referring now to FIG. 1, numeral 1 denotes a filter coefficients recording section, numeral 2 a convolution section, numeral 10 a noise source, numeral 11 a pick-up circuit for picking up a noise, numerals 12 and 16 an analogue-to-digital converter (A/D), numeral 13 a digital-to-analogue converter (D/A), numeral 14 a speaker, numeral 7 an adaptive filter, numeral 8 a transmission characteristic compensation section, and numeral 9 a tap value updating section for updating a tap value of the filter 7.

First, before describing the noise reduction system according to the present invention, operations of the noise reduction system without the filter coefficients recording section 1 and the convolution section 2 according to the prior art will be described.

The microphone 15 is disposed at a position where a noise is to be reduced. The adaptive filter 7 corrects a difference between a signal picked-up at the pick-up circuit and a noise inputted to the microphone 15 from the noise source 10 and the corrected difference is transmitted from the speaker 14. At this time the signal transmitted from the speaker 14 has the same amplitude as and the reversed phase to the noise from the noise source 10.

The adaptive filter 7 is composed of digital filters having a delay line with tap, as will be described hereinafter in FIG. 2. That is to say, by inputting an output signal of the pick-up circuit which has a correlation with a noise, the adaptive filter 7 determines a transmission characteristic of the filter such that the sound pressure and the wave shape from the adaptive filter 7 has a reversed phase to the noise at the position of the microphone 15. This adaptation process is performed at the tap value updating section 9.

The transmission characteristic compensation section 8 transmits a compensation signal having the same amplitude as and a reversed phase to the signal from the noise source 10 so as to compensate a transmission characteristic being subjected to the effect of a delay time or a band restriction while the signal generated in the adaptive filter 7 passes through the D/A converter 13 and the speaker 14 and reaches the microphone 15.

Figure 3:
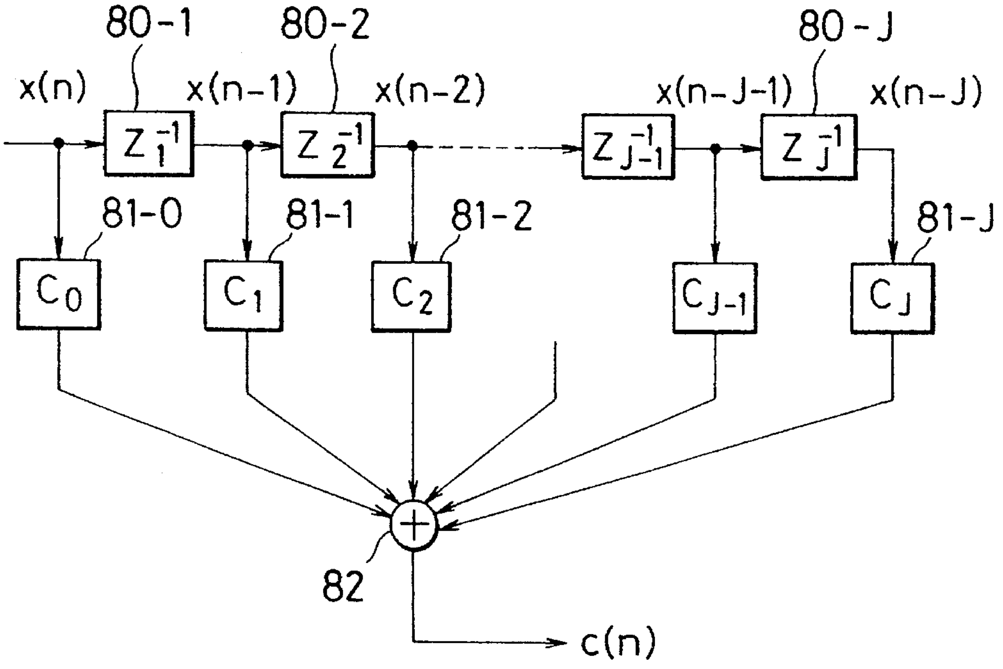
FIG. 3 is a circuit diagram showing an example of a transmission characteristic compensation section according to an embodiment.

This transmission characteristic can also be composed of digital filters having a delay line with tap. FIG. 3 illustrates a composition of the transmission characteristic compensation section 8. Numeral 80-1 to 80-J denote delay elements for delaying a time corresponding to a sampling interval of the sampling pulse inputted to A/D converters 12 and 16. Further, numeral 81-0 to 81-J are tap values by which the output value of the delay element is multiplied and the multiplied output value is outputted therefrom, Where the output value of the A/D converter 12 is x (n) at $t=t_n$ and x (n+1) at $t=t_{n+1}$, and where $<i=1, 3>\Sigma x_i=x_1+x_2+x_3$, The composition signal C (n) is:

$$C(n)=<i=0,\ J>R\times(n-i)C_i \quad (1)$$

Figure 2:
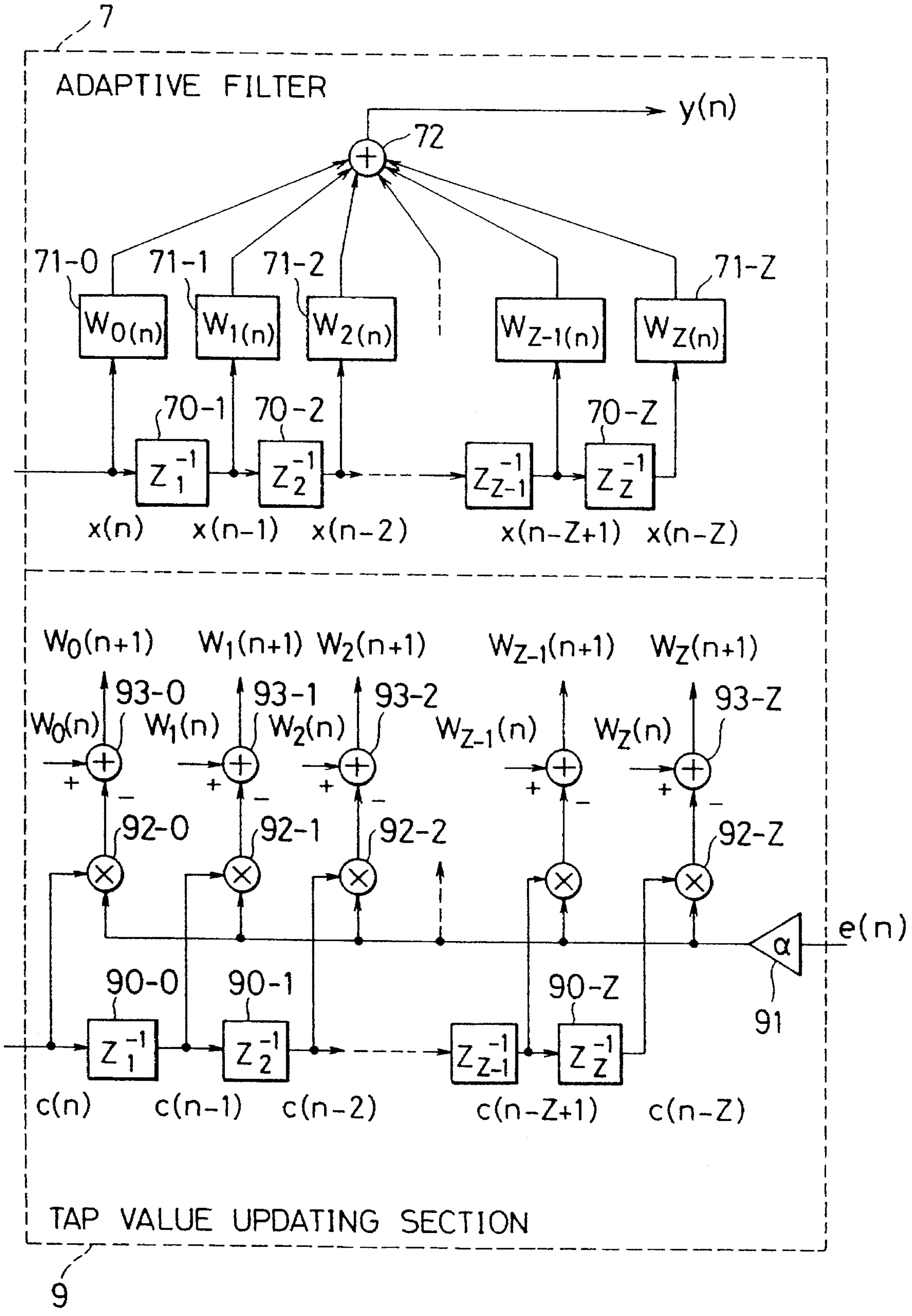
FIG. 2 is a circuit diagram showing an example of an adaptive filter and a tap value updating section according to an embodiment.

Referring to FIG. 2, the adaptive filter 7 comprises delay elements 70-1 to 70-Z, tap values 71-O to 71-Z and an adder 72. The delay element 70 delays an output signal from the A/D converter 12 by the time equal to the interval of the sampling pulse.

Therefore, the output y (n) from the adaptive filter 7 is:

$$y(n)=<i=0,\ Z>\Sigma x(n-i)W_i(n) \quad (2)$$

Then y (n) is converted into an analogue signal in the D/A converter 13 and transmitted from the speaker 14.

Tap values of the adaptive filter $W_0$ (n) to $W_Z$ (n) are updated each time the sampling pulse is generated. The updating of the tap value is performed at the tap value updating section 9. Tap value updating section 9 comprises multipliers 90, 91 and 92, and an adder 93, as referring to FIG. 2.

In the delay element 90, the output signal C (n) from the transmission characteristic compensation section 8 is inputted and propagated after being delayed by a time equal to the interval of the sampling pulse. Further, the multiplier 91, the output e (t) of the microphone 15 is multiplied by α which has been predetermined by the loop characteristic of the adaptive control system.

Next, the updating value W (n+1) of the adaptive filter 7 for each tap value will be calculated. For making explanation easier, an example of the case where the tap value $W_0$ (n) of the tap 71-0 is updated into $W_0$ (n+1) will be explained.

In the multiplier 92-0 the output of the multiple 91 is multiplied by the output value C (n) from the transmission characteristic compensation section 8. Further, in the adder 93-0 the output value from the multiplier 92-0 is reduced from the tap value $W_0$ (n) at $t=t_n$ and the result becomes an updating value $W_0$ (n+1) at $t=t_{n+1}$.

That is to say:

$$W_0(n+1)=W_0(n)-\alpha C(n)e(n) \quad (3)$$

Further, with respect to other tap value $W_i$, updating is made as follows:

$$W_i(n+1)=W_i(n)-\alpha C(n-i)e(n) \quad (4)$$

As described above, by means of updating the tap value, the sound transmitted from the speaker 14 becomes a sound signal having the same as and the reversed phase to the noise from the noise source 10 at the input of the microphone 15, whereby the noise in the vicinity of the microphone is reduced.

Figure 5:
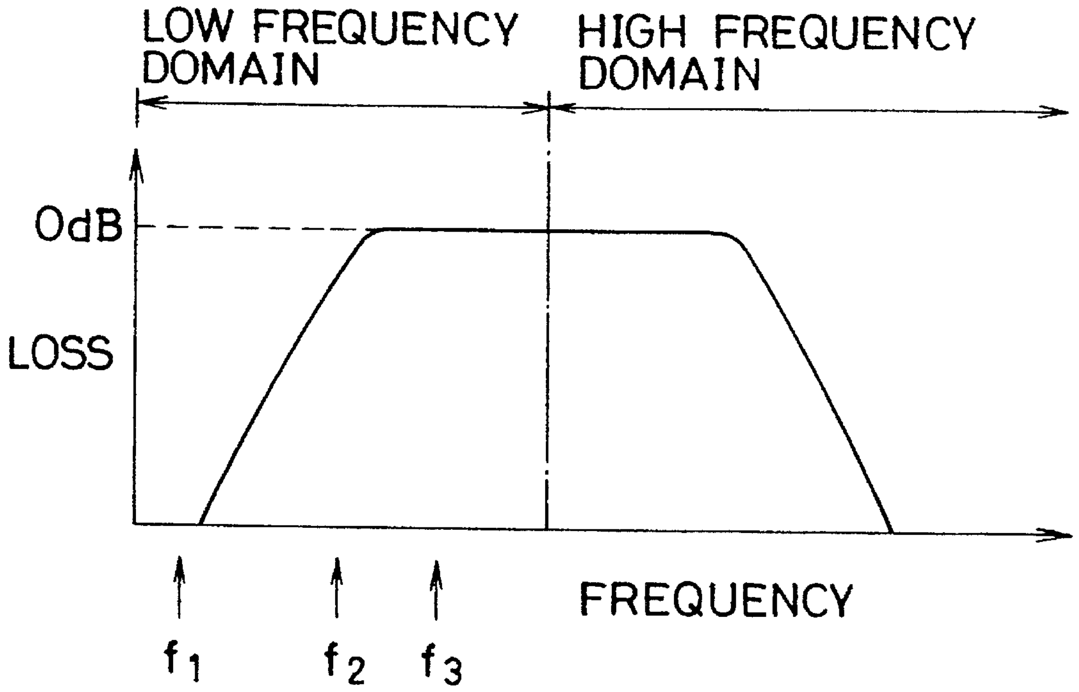
FIG. 5 is a graph showing a frequency characteristic of a speaker according to an embodiment.

The noise reduction described above is operated only when the characteristic of the speaker 14 for converting an electric signal into a sound signal is within a proper range. That is if the loss characteristic of the speaker in converting electric signals into sound signals has a characteristic for example as shown in FIG. 5, the noise can be reduced properly with respect to a noise of a frequency $f_3$ existing in a frequency band having a flat conversion loss characteristic.

However, with respect to a noise of a frequency $f_1$ existing in a frequency band having a large conversion loss characteristic, the signal generated from the adaptive filter 7 for canceling the noise of a frequency $f_1$ can not be converted into a sound and as a result an error signal having a frequency component is outputted from the microphone 15.

Because of this, the tap value of the adaptive filter 7 becomes larger and larger with an accumulation of the error signals and eventually distortion will occur due to a saturation of an amplifier (not shown) to drive the speaker and sometimes the system would diverge due to an overflow of the capacity of the memory for memorizing tap values. With respect to a noise having a frequency $f_2$, if the amplifier and the speaker are operated to the utmost of their capacities, the noise can be reduced at an acceptable level.

To solve these problems, the noise reduction system according to the present invention is furnished with the filter coefficients recording section and the convolution section 2. The operational principle for these equipment's will be described next.

As described before, the reason why the noise reduction system becomes unstable is that a noise having frequency components not existing in the reproducing band width of the speaker 14 is produced from the noise source 10 and since these components can not be canceled by the input of the microphone 15, the error signals are outputted.

Consequently, the way for making the system stable 18 can be achieved by eliminating the components incapable of being canceled among the error signals e (n) which are inputted to the tap value updating section 9. Thus the system can be made stable by means of inserting a filter having the same frequency characteristic as the speaker 14 into the output of the microphone 15 and inputting the output of the filter inserted to the tap value updating section 9 as an error signal.

As a practical problem, since it makes the composition of the system more complicated to insert the filter into the microphone 15, in an embodiment of the present invention the adaptive filter 7 serves as a filter for this purpose too. That is to say, in order to combine two filters connected in series into one filter the present invention introduces such a way that each filter coefficient value is convoluted into a new filter coefficient, For this purpose the filter coefficients having the same conversion characteristic as the speaker 14 have been recorded in the filter coefficients recording section I beforehand. The convolution section 2 convolutes a filter coefficient F recorded in the filter coefficients recording section 1 into a tap value W formed in the tap value updating section 9 of the adaptive filter 7 to establish a new tap value of the adaptive filter 7.

Where the tap value $W_i$ (n+1) formed by the formula (4) in case of no convolution section 2 is expressed as $w_i(n+1)$ and the value recorded in the filter coefficients recording section 1 of the filter coefficient is m, the k th tap value $W_k$ (n+1) is:

$$W_k(n+1)=<j=1,\ m>\Sigma w_{t+j}(n+1)F_j \quad (5)$$

$$\text{where } t=k-(m+1)/2 \ (m \text{ is an odd number}) \quad (6)$$

$$\text{where } t=k-m/2 (m \text{ is an even number}) \quad (7)$$

Figure 4:
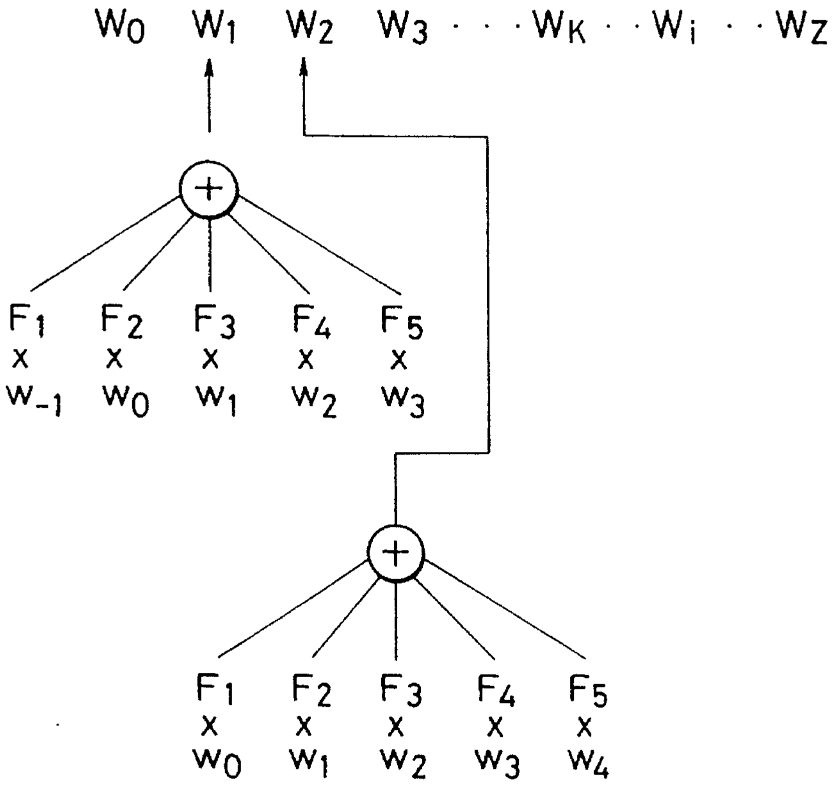
FIG. 4 is a drawing showing a convolution section according to an embodiment.

Next, referring to FIG. 4, the convolution calculation according to the formula (5) will be described for the case of m=5.

There are tap values $W_0$ to $W_Z$in the adaptive filter 7 as shown in FIG. 7. Further, there are tap values $w_0$to $w_Z$ formed in the tap value updating section 9. Since m is 5, t is t=k−3 from the formula (7). In case of k=1, according to the formula (5), the tap value $W_1$ is:

$$W_1=w_{-1}F_1+w_0F_2+w_1F_3+w_2F_4+w_3F_5 \quad (8)$$

Further, in case of k=2 the tap value W2 is:

$$W_2=w_0F_1+w_1F_2+w_2F_3+w_3F_4+w_4F_5 \quad (9)$$

In the above formula, since $w_{-1}$ is not formed in the tap value updating section 9, the first term of the formula (8) is nil. The relation between formulas (8) and (9) is shown in FIG. 4 in which the tap value $W_k$ is calculated by corresponding $w_k$to the center value $F_{(m+1)/2}$ of the filter coefficient F.

Thus, by recording this newly formed tap value $W_k$in the memory of the adaptive filter 7 and operating it, a signal of the frequency component which has been cut by the speaker 14 is no more outputted from the adaptive filter.

The way of convolution of the filter coefficient into the tap value is not limited to the one shown in this embodiment of the present invention.

Further, by recording a plurality of sets of the filter coefficients having a different characteristic respectively in the filter coefficients recording section 1, it becomes possible to select a filter coefficient having similar characteristic to a specific speaker from these sets of the filter coefficients, whereby the replacement of speakers can be done without any modification of the system.

Further, in the embodiment of the present invention the filter coefficients are formed such that they have the same characteristic as the speaker, however it is not always necessary to give exactly the same characteristic as the speaker. For practical purposes, it is allowable if the characteristic of the filter is similar to the characteristic of the speaker. For example, when a signal of the frequency $f_2$ passes through the inserted filter, the noise can be reduced by generating a larger signal than the signal generated corresponding to the frequency $f_3$. Consequently, the similarity of the filter characteristic to the speaker characteristic can be allowed to the extent that the system is not saturated.

Further, in this embodiment it is constituted such that the inserted filter passes through both low and high frequency domains, however in applying the system to an actual automobile, the internal noise generated by the engine revolution is primarily composed of a low frequency domain and the composition of high frequency is minor or does not last long if any.

Consequently, the filter characteristic for stabilizing the system can be allowed to limited be to a low frequency domain and it has been confirmed in an actual use that the noise reduction system limited to a low frequency is operated with a good stability.

Summarizing the effect of the present invention, since the noise reduction system according to the present invention is charaterized in forming a tap value of the adaptive filter by convoluting a filter coefficient having a similar pass characteristic to the speaker frequency characteristic into a tap value formed by the adaptive control of the adaptive filter, a signal whose frequency band makes the system unstable is cut off from the system, whereby it is possible to operate the noise reduction system stably.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. A vehicle internal noise reduction system having, pick-up means for picking up a noise signal from a sound source and for producing a pick-up signal, an adaptive filter for forming a tap value and for generating a canceling signal, a speaker with predetermined frequency characteristics for generating a canceling sound in order to cancel an internal noise in a passenger compartment of a vehicle, a microphone provided in said passenger compartment for receiving said canceling sound and said internal noise and for outputting an error signal as a result of a difference between said canceling sound and said internal noise, transmission characteristics compensation means responsive to said pick-up signal for compensating transmission characteristics of a propagation path between said adaptive filter and said microphone and for producing a compensation signal, and tap value updating means for updating said tap value in accordance with said error signal and said compensation signal and for transmitting an updated tap value to said adaptive filter, comprising:

filter coefficient recording means for recording a filter coefficient with similar band pass characteristics to said predetermined frequency characteristics of said speaker and for generating a coefficient signal; and convolution means responsive to said coefficient signal for convoluting said filter coefficient into said tap value by calculating a sum of convolution products in order to coincide said tap value to be calculated with a center value of said filter coefficients recorded in said filter coefficient recording means and to delete a frequency component existing in said predetermined frequency characteristics of said speaker from said canceling sound so as to perform a stable operation of said noise reduction system.

2. The system according to claim 1, wherein said band pass characteristic of said filter coefficient has at least a low frequency domain.

3. The system according to claim 1, wherein said band pass characteristic of said filter coefficient has a plurality of sets of characteristics so as to select an optimum pass characteristic for each of various speakers.

4. A method of reducing internal noise in a vehicle having, pick-up means for picking up a noise signal from a sound source and for producing a pick-up signal, an adaptive filter for forming a tap value and for generating a canceling signal, a speaker with predetermined frequency characteristics for generating a canceling sound in order to cancel an internal noise in a passenger compartment of a vehicle, a microphone provided in said passenger compartment for receiving said canceling sound and said internal noise and for outputting an error signal as a result of a difference between said canceling sound and said internal noise, transmission characteristics compensation means responsive to said pick-up signal for compensating transmission characteristics of a propagation path between said adaptive filter and said microphone and for producing a compensation signal, and tap value updating means for updating said tap value in accordance with said error signal and said compensation signal and for transmitting an updated tap value to said adaptive filter, comprising:

recording a filter coefficient with similar band pass characteristics to said predetermined frequency characteristics of said speaker;

convoluting said filter coefficient into said tap value by calculating a sum of convolution products in order to coincide said tap value to be calculated with a center value of said filter coefficients recorded in said filter coefficient recording means and to delete a frequency component existing in said predetermined frequency characteristics of said speaker from said canceling sound so as to effectively reduce said internal noise in said vehicle.

* * * * *